US010655818B2

(12) United States Patent
Callahan (10) Patent No.: US 10,655,818 B2
(45) Date of Patent: May 19, 2020

(54) LIGHT-CONVERTING LIGHTING ASSEMBLY

(71) Applicant: THE BOEING COMPANY, Chicago, IL (US)

(72) Inventor: Kevin S. Callahan, Shoreline, WA (US)

(73) Assignee: THE BOEING COMPANY, Chicago, IL (US)

( * ) Notice: Subject to any disclaimer, the term of this patent is extended or adjusted under 35 U.S.C. 154(b) by 548 days.

(21) Appl. No.: 15/413,495

(22) Filed: Jan. 24, 2017

(65) Prior Publication Data

US 2018/0209613 A1    Jul. 26, 2018

(51) Int. Cl.
*F21V 14/08* (2006.01)
*F21V 9/30* (2018.01)
(Continued)

(52) U.S. Cl.
CPC .................... *F21V 9/30* (2018.02); *A61L 2/10* (2013.01); *A61L 2/24* (2013.01); *B64D 11/02* (2013.01);
(Continued)

(58) Field of Classification Search
CPC ...... F21V 9/30; B64F 5/30; A61L 2/24; A61L 2/0047; A61L 2/10; A61L 1/02;
(Continued)

(56) References Cited

U.S. PATENT DOCUMENTS

| 4,819,276 A | 4/1989 | Stevens |
| 8,761,565 B1 | 6/2014 | Coleman |

(Continued)

FOREIGN PATENT DOCUMENTS

| GB | 2527964 | 1/2016 |
| JP | H07289616 | 11/1995 |

(Continued)

OTHER PUBLICATIONS

Extended European Search Report for EP 17203770.7-1010, dated Feb. 6, 2018.

*Primary Examiner* — Medhat Badawi
*Assistant Examiner* — Vicente Rodriguez
(74) *Attorney, Agent, or Firm* — The Small Patent Law Group LLC; Joseph M Butscher (57) ABSTRACT

A lighting assembly is configured to selectively emit light at a first frequency and light at a second frequency. The lighting assembly includes a light source that is configured to emit the light at the first frequency over a light emission path, a light converter, and an actuator operatively coupled to the light source or the light converter. The actuator is configured to move the light converter or the light source relative to the other of the light converter or the light source between a first position and a second position. The light converter is within the light emission path in the first position, and outside of the light emission path in the second position. The light converter converts the light at the first frequency to the light at the second frequency in the first position, and wherein the light at the first frequency is emitted from the lighting assembly when the light converter is in the second position.

19 Claims, 8 Drawing Sheets

(51) Int. Cl.
*A61L 2/10* (2006.01)
*B64D 11/02* (2006.01)
*A61L 2/24* (2006.01)
*B64F 5/30* (2017.01)

(52) U.S. Cl.
CPC ............. *B64F 5/30* (2017.01); *A61L 2202/14* (2013.01); *A61L 2202/25* (2013.01); *Y02T 50/46* (2013.01)

(58) Field of Classification Search
CPC .. A61L 2202/14; A61L 2202/25; Y02T 50/46; B64D 11/02; B64D 47/02
USPC .................. 250/492.1, 493.1, 504 R; 422/24
See application file for complete search history.

(56) References Cited

U.S. PATENT DOCUMENTS

| | | | | |
|---|---|---|---|---|
| 9,783,974 | B1* | 10/2017 | Tillotson | ................. E03D 9/002 |
| 9,993,571 | B2* | 6/2018 | Lin | ........................... A61L 2/10 |
| 2006/0261291 | A1* | 11/2006 | Gardner, III | ........... A01K 63/06 |
| | | | | 250/504 R |
| 2010/0320405 | A1* | 12/2010 | Gardner, III | ............. G01J 3/10 |
| | | | | 250/504 H |
| 2014/0059796 | A1* | 3/2014 | Boodaghians | ............ A61L 2/10 |
| | | | | 15/339 |
| 2014/0115764 | A1 | 5/2014 | Cheng | |
| 2016/0220716 | A1 | 8/2016 | Childress | |

FOREIGN PATENT DOCUMENTS

| WO | WO 2014036217 | 3/2014 |
|---|---|---|
| WO | WO 2016/105347 | 6/2016 |

* cited by examiner

LIGHT-CONVERTING LIGHTING ASSEMBLY

FIELD OF THE DISCLOSURE

Embodiments of the present disclosure generally relate to lighting assemblies, and, more particularly, to lighting assemblies that are configured to selectively convert light at a first frequency (such as an ultraviolet light frequency) to a second frequency (such as a visible light frequency) that is lower than the first frequency.

BACKGROUND OF THE DISCLOSURE

Commercial aircraft are used to transport passengers between various locations. A typical commercial aircraft includes one or more lavatories within an internal cabin.

Systems are currently being developed to disinfect or otherwise sanitize surfaces within aircraft lavatories that use ultraviolet (UV) light. For example, it has been found that far UV light efficiently disinfects exposed surfaces within a lavatory.

In order to effectively sanitize a surface within a lavatory, a UV light assembly may be fixed in close proximity to the surface. For example, a UV light assembly may be spaced from a toilet within a lavatory a distance of less than one foot. As can be appreciated, however, positioning a UV light assembly within close proximity to a component may interfere with use of the component. In general, a UV light assembly should not expose passengers to harmful UB light, nor undesirably protrude into a confined space of an aircraft lavatory.

In order for certain known UV light sources to operate effectively, such light sources warm up after being activated. For example, certain UV light sources may warm up for at least thirty seconds before generating UV light that effectively sanitizes a surface. However, the sanitation cycle may last only two to three seconds. As such, the warm-up times for certain UV light sources is often far longer than the actual time of sanitation.

Further, many UV light sources are relatively large and bulky, and may be difficult to integrate into a confined space of an aircraft lavatory. For example, incorporating a UV light source within the confined space of the lavatory that already includes a visible light source may prove difficult.

SUMMARY OF THE DISCLOSURE

A need exists for a system and method for efficiently and effectively sanitizing a surface of a component. A need exists for a system and method for operating a UV light assembly to sanitize a component without interfering with use of the component by an individual. Further, a need exists for a system and method for efficiently and effectively incorporating a UV light assembly into a confined space of an aircraft lavatory.

With those needs in mind, certain embodiments of the present disclosure provide a lighting assembly that is configured to selectively emit light at a first frequency and light at a second frequency. The lighting assembly includes a light source that is configured to emit the light at the first frequency over a light emission path, a light converter, and an actuator operatively coupled to one of the light source or the light converter. The actuator is configured to move the light converter or the light source relative to the other of the light converter or the light source between a first position and a second position. The light converter is within the light emission path in the first position, and outside of the light emission path in the second position. The light converter converts the light at the first frequency to the light at the second frequency in the first position. The light at the first frequency is emitted from the lighting assembly when the light converter is in the second position.

In at least one embodiment, the second frequency is lower than the first frequency. For example, the light at the first frequency may be ultraviolet (UV) light, while the light at the second frequency may be visible light.

In at least one embodiment, the actuator is operatively coupled to the light converter, and the light source is fixed in place. Optionally, the actuator is operatively coupled to the light source, and the light converter is fixed in place.

In at least one embodiment, the actuator is configured to rotatably or pivotally move one of the light converter or the light source relative to the other of the light converter or the light source. In at least one other embodiment, the actuator is configured to linearly move one of the light converter or the light source relative to the other of the light converter or the light source.

In at least one embodiment, the light converter includes an optically transparent substrate and a phosphor layer. The phosphor layer is configured to down-convert the light at the first frequency to the light at the second frequency. The phosphor layer may coat at least a portion of the substrate. Optionally, the phosphor layer may be dispersed throughout the substrate. In at least one embodiment, the phosphor layer is protected inside the substrate.

Certain embodiments of the present disclosure provide a method of operating a lighting assembly to selectively emit light at a first frequency and light at a second frequency. The method includes emitting the light at the first frequency from a light source over a light emission path, and using an actuator operatively coupled to one of the light source or the light converter to move one of the light converter or the light source relative to the other of the light converter or the light source between a first position and a second position. The light converter is within the light emission path in the first position, and outside of the light emission path in the second position. The method may also include converting the light at the first frequency with the light converter in the first position to the light at the second frequency, and emitting the light at the first frequency from the lighting assembly when the light converter is in the second position.

Certain embodiments of the present disclosure provide a vehicle that includes an internal cabin, and a lavatory within the internal cabin. The lavatory includes a floor that supports a toilet and a sink. At least on ultraviolet (UV) light sanitizing system is configured to sanitize at least one surface of the floor, the toilet, or the sink. The UV light sanitizing system(s) includes a lighting assembly that is configured to selectively emit sanitizing UV light and visible light. The lighting assembly includes a light source that is configured to emit the UV light over a light emission path, a light converter, and an actuator operatively coupled to one of the light source or the light converter. The actuator is configured to move one of the light converter or the light source relative to the other of the light converter or the light source between a first position and a second position. The light converter is within the light emission path in the first position, and outside of the light emission path in the second position. The light converter converts the sanitizing UV light to the visible light in the first position. The sanitizing UV light is emitted from the lighting assembly when the light converter is in the second position.

A UV light control unit is in communication with the UV light assembly. The UV light control unit is configured to control operation of the actuator to selectively emit the sanitizing UV light and the visible light from the UV light assembly. The UV light control unit is configured to operate the UV light assembly during a sanitizing cycle in which the UV light assembly emits the sanitizing UV light onto the surface(s) to sanitize the surface(s).

The UV light sanitizing system may also include one or more presence sensors within the lavatory and in communication with the UV light control unit. The presence sensors are configured to detect a presence of an individual within the lavatory. The UV light control unit maintains the light converter in the first position when the lavatory is occupied.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Certain embodiments of the present disclosure provide a lighting assembly that is configured to selectively generate light at different frequencies. The lighting assembly is configured to generate light at a first frequency and a second frequency that is lower than the first frequency. The light at the first frequency may be ultraviolet (UV) light that is used to sanitize a surface of a component, such as within an aircraft lavatory. The light at the second frequency may be visible light that is used to illuminate the aircraft lavatory when occupied by an individual. Optionally, the light at the first frequency may be other than ultraviolet light, and the light at the second frequency may be other than visible light. For example, the light at the first frequency may be visible light, while the light at the second frequency may be infrared light.

In at least one embodiment, the lighting assembly includes an actuator that is configured to move one of a light source or light converter relative to the other. The light converter may include an optically transparent substrate. The substrate may be coated, lined, or otherwise coupled to a phosphor layer. When the light converter is disposed within a light emission path of the light source, the light converter converts the light emitted from the light source to a lower frequency.

For example, the light source may be a UV light source that emits UV light. As the UV light impinges on the light converter, the UV light excites the phosphor layer to a higher state. In the process, the UV light passing through the light converter loses energy, and is converted to a lower frequency, such as that of visible light, which is then used to safely and efficiently illuminate a space without the need for an additional visible light source. During a sanitation process, for example, the light converter is moved out of the light emission path, so that the UV light as emitted from the UV light source passes through a light outlet passage (such as an opening, aperture, clear window, or the like) towards a component within a space that is to be sanitized.

Figure 1:
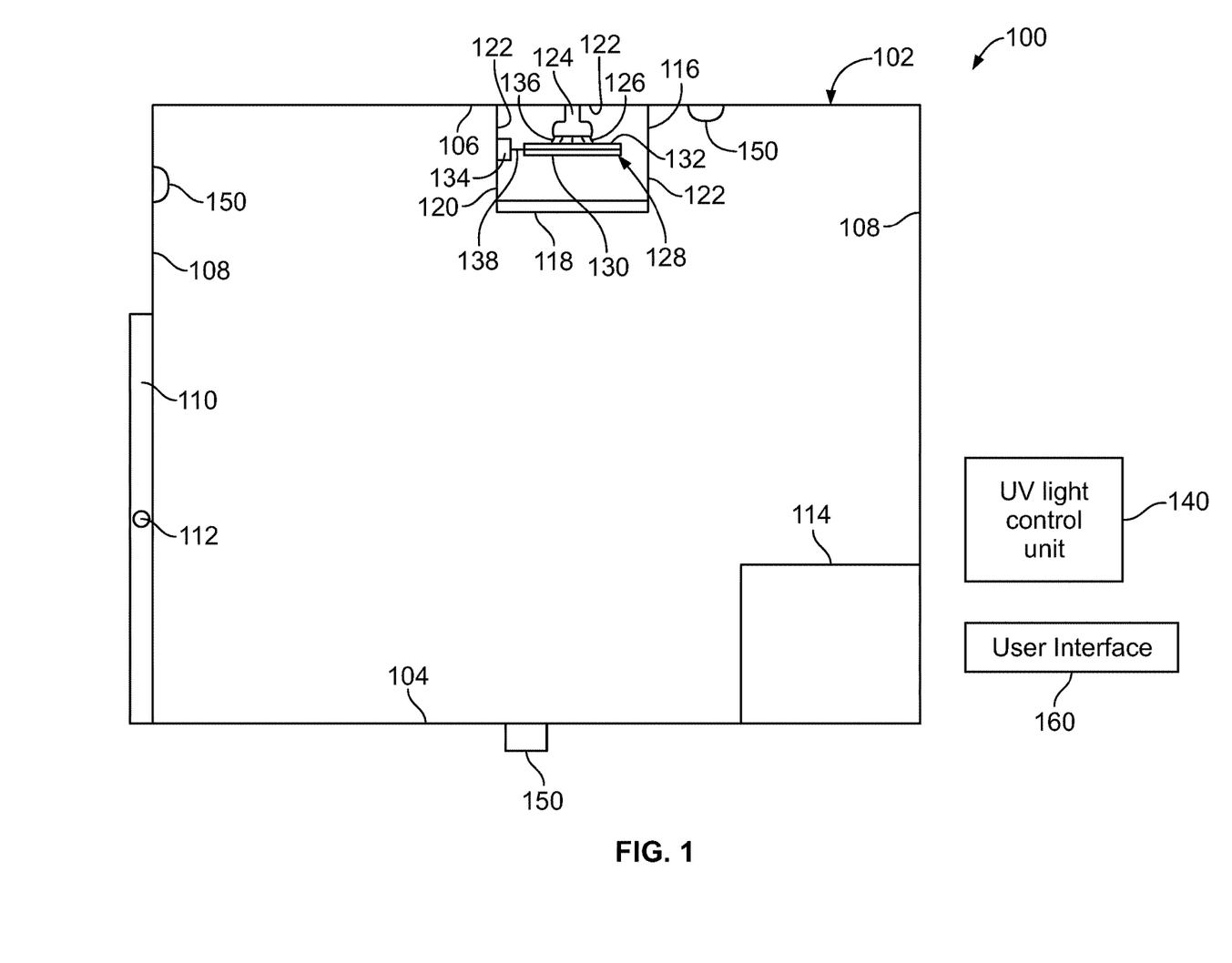
FIG. 1 illustrates a schematic diagram of an ultraviolet light sanitizing system for an enclosed space, according to an embodiment of the present disclosure.

FIG. 1 illustrates a schematic diagram of a UV light sanitizing system 100 for an enclosed space 102, according to an embodiment of the present disclosure. The enclosed space 102 may be defined by a floor 104, a ceiling 106, and walls 108 extending between the floor 104 and the ceiling 106. A door 110 may be moveably secured to one of the walls 108. The door 110 may include a lock 112 that is configured to securely lock the door 110 in a closed position. When the lock 112 is in a locked position, the door 110 is unable to be opened. When the lock 112 is in an unlocked position, the door 110 may be opened. The enclosed space 102 may be a confined space onboard a commercial aircraft. For example, the enclosed space 102 may be a lavatory onboard an aircraft. As another example, the enclosed space 102 may be a galley onboard an aircraft. As yet another example, the enclosed space 102 may be a passenger area onboard an aircraft. The enclosed space 102 may or may not include the door 110. The enclosed space 102 may be within various other vehicles, structures, and/or the like. For example, the enclosed space 102 may be a room within a commercial, municipal, or residential building, or a room onboard a train, bus, ship, or the like.

The enclosed space 102 may include at least one component 114 to be sanitized (for example, disinfected, sterilized, or otherwise cleaned) after use. For example, the component 114 may be a toilet, sink, floor, cabinet, and/or the like within a lavatory of an aircraft.

The UV light sanitizing system 100 includes a lighting assembly 116, which may be secured to the ceiling 106. For example, the lighting assembly 116 may extend below the ceiling 106. In at least one other embodiment, a light outlet passage 118 (such as an open end, aperture, clear window, or the like) is flush with or recessed within a lower surface of the ceiling 106. Optionally, the lighting assembly 116 may be secured to (or supported by) various other structures of the enclosed space 102, such as the floor 104, walls 108, a portion of the component 114, or the like.

The lighting assembly 116 includes a housing 120, which may include opaque outer walls 122 connected to the light outlet passage 118. A light source 124 is secured within the housing 120. The light source 124 is configured to emit light 126 at a first frequency, such as ultraviolet light.

The lighting assembly 116 also includes a light converter 128. The light converter 128 includes an optically-transparent substrate 130 (such as a transparent plastic, glass, or the like panel) that is coupled to a phosphor layer 132. The phosphor layer 132 may be secured over or under the substrate 130. For example, the phosphor layer 132 may coat an entirety of the substrate 130. In at least one other embodiment, the phosphor layer 132 may coat an upper or lower surface of the substrate 130. In at least one other embodiment, the phosphor layer 132 may be dispersed throughout the substrate 130 (for example, mixed into the substrate 130). In another embodiment, the substrate 130 may be one or more transparent pieces of plastic or glass, and the phosphor layer 132 may be disposed within the substrate 130, such as within an interior channel, thereby protecting the phosphor layer 132 from dust, dirt, debris, and damage.

The light converter 128 is coupled to an actuator 134, which may be contained within, secured to an outer portion of, or remotely located from the housing 120. The actuator 134 is configured to move the light converter 128 between a first position, in which the light converter 128 is within a light emission path 136 of the light source 124, and a second position, in which the light converter 128 is outside of the light emission path 136 of the light source 124.

The actuator 134 may connect to the light converter 128 through a link 138 that allows the actuator 134 to move the light converter 128 between the first and second positions. The actuator 134 may be an electric motor, a pneumatic motor, a hydraulic motor, one or more solenoids, one or more pistons, and/or the like. The actuator 134 may be configured to rotate the light converter 128 between the first and second positions. In at least one other embodiment, the actuator 134 may be configured to pivot the light converter 128 between the first and second positions. In at least one other embodiment, the actuator 134 may be configured to linearly move the light converter 128 between the first and second positions.

Optionally, the actuator 134 may be operatively coupled to the light source 124, while the light converter 128 remains in a fixed position within the housing 120. In this embodiment, the actuator 134 is configured to move the light source 124 between first and second positions relative to the light converter 128.

The lightning system 116 may be controlled by a UV light control unit 140. For example, the UV light control unit 140 may be in communication with the actuator 134 and the light source 124 such as through wired or wireless connections. The UV light control unit 140 may be positioned within or connected to the enclosed space 102, or may be remotely located therefrom. In at least one embodiment, the UV light control unit 140 is housed within the lighting assembly 116. The UV light control unit 140 is configured to control operation of the lighting assembly 116 to selectively emit sanitizing UV light into the enclosed space and illuminating visible light that illuminates an interior of the enclosed space 102.

During a sanitizing cycle or mode, the UV light control unit 140 operates the actuator 134 to move the light converter 128 outside of a light emission path 136 of the UV light source 124, which emits the UV light 126. As such, UV light passes through the light outlet passage 118 and onto the component 114. Upon completion of the sanitizing cycle, the UV light control unit 140 operates the actuator 134 to move the light converter 128 back within the light emission path 136 of the UV light source 124.

When the light converter 128 is disposed within the light emission path 136, the light converter 128 down-converts the UV light 126 emitted from the UV light source 124 to a lower frequency. In particular, as the UV light 126 impinges on the light converter 128, the UV light 126 excites the phosphor layer 132 to a higher energy state. In the process, the UV light 126 passing through the light converter loses energy, and is converted to lower frequency visible light, which safely and efficiently illuminates the interior of the enclosed space 102 without the need for an additional visible light source.

The light source 124 may include one or more UV light elements, such as an arc lamp(s), laser(s), light emitting diode(s) (LEDs), microfilament(s), fiber optic element(s), bulb(s), and/or the like. In at least one embodiment, the light source 124 emits the UV light 126 as far UV light that is used to sanitize the component 114. Alternatively, the UV light 126 may be UVA light, UVB light, UVC light, vacuum UV light, or the like. In at least one embodiment, the light source 124 may include UV light elements that are configured to emit UV light with different UV bands (for example, at different wavelengths and different frequencies). For example, one UV light element may be configured to emit far UV light, while another UV light element may be configured to emit UVC light.

One or more presence sensors 150 may be secured within the enclosed space 102. The presence sensors 150 may be ultrasound sensors, infrared sensors, thermal sensors, weight sensors (for example, weight scales), and/or the like that are configured to detect the presence of an individual within the enclosed space 102. In at least one embodiment, at least one presence sensor 150 may be a digital scale that detects the presence of an individual through a discernable detection of mass or weight within the enclosed space 102. The presence sensors 150 are in communication with the UV light control unit 140 through one or more wired or wireless connections. Based on presence signals received from the presence sensors 150, the UV light control unit 140 determines whether or not an individual is within the enclosed space 102. When the UV light control unit 140 determines that an individual is within the enclosed space, the UV light control unit 140 refrains from operating the lighting assembly 116 to emit sanitizing UV light into the enclosed space. Instead, when an individual is within the enclosed space, the UV light control unit 140 ensures that the light converter 128 is within the light emission path 136 of the light source 124, which down-converts the emitted UV light into visible light (as described above), thereby safely illuminating the interior of the enclosed space 102.

Optionally, the enclosed space 102 may not include the presence sensors 150. Instead, the UV light control unit 140 may be configured to determine that the enclosed space is unoccupied, such as by being in communication with the lock 112 and/or the component 114. For example, the UV light control unit 140 may determine that the enclosed space 102 is unoccupied when the door 110 is locked. The UV light control unit 140 may initiate a sanitizing cycle based on a sequence of events, which may be triggered by the component 114 being used, the door being unlocked, and the door being subsequently closed. During the sanitizing cycle, the UV light control unit 140 may ensure that the door 110 is locked, so that individuals may not enter the enclosed space 102. As the sanitizing cycle completes, the UV light control unit 140 moves the light converter 128 back into the light emission path 136 of the light source 124 so that light emitted from the light source 124 is down-converted by the phosphor layer 132 into safe, visible light, and then the UV light control unit 140 unlocks the door 110. In at least one embodiment, if the door 110 is opened, and/or the presence sensors 150 detect the presence of an individual within the enclosed space 102 during a sanitizing cycle, the UV light control unit 140 may immediately move the light converter 128 into the light emission path 136, and/or deactivate the light source 124.

The UV light control unit 140 may initiate the sanitizing cycle after each use of the enclosed space 102 (such as after each time the door 110 is locked and unlocked, and/or after each time the presence sensors 150 detect that an individual has left the enclosed space 102). Optionally, the sanitizing cycle may be initiated after a predetermined number of uses of the enclosed space 102, such as after each second, third, fourth, fifth, or nth use.

The UV light control unit 140 may also be in communication with a user interface 160, such as a computing device (for example, a computer, handheld smart device, dedicated control panel, or the like) that allows an individual (such as a flight attendant onboard an aircraft) to initiate the sanitizing cycle. Optionally, the UV light sanitizing system 100 may not include the user interface 160.

While the UV light sanitizing system 100 is shown with a single lighting assembly 116, additional lighting assemblies may be used. For example, the UV light sanitizing system 100 may include two, three, four, or more lighting assemblies in communication with the UV light control unit 140. Each lighting assembly may be configured to sanitize a different (or the same) surface within the enclosed space 102. For example, one lighting assembly 116 may be configured to sanitize a surface of a toilet, another UV light assembly may be configured to sanitize a sink, while another lighting assembly may be configured to sanitize at least a portion of the floor 104.

Alternatively, the lighting assembly 116 may be used in various other settings. In at least one embodiment, the light source 124 may be configured to emit light at a different frequency than UV light. For example, the light source 124 may be configured to emit visible light, and the phosphor layer 132 may convert the emitted visible light to a lower frequency, such as infrared light. The lighting assembly 116 may be used with respect to applications other than sanitation. For example, the lighting assembly 116 may be used to selectively convert visible light to infrared light with respect to night vision goggles, in which the lighting assembly 116 may or may not include a light source.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the UV light control unit 140 may be or include one or more processors that are configured to control operation of the lighting assembly 116, as described above.

The UV light control unit 140 is configured to execute a set of instructions that are stored in one or more data storage units or elements (such as one or more memories), in order to process data. For example, the UV light control unit 140 may include or be coupled to one or more memories. The data storage units may also store data or other information as desired or needed. The data storage units may be in the form of an information source or a physical memory element within a processing machine.

The set of instructions may include various commands that instruct the UV light control unit 140 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the UV light control unit 140. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the UV light control unit 140 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 2:
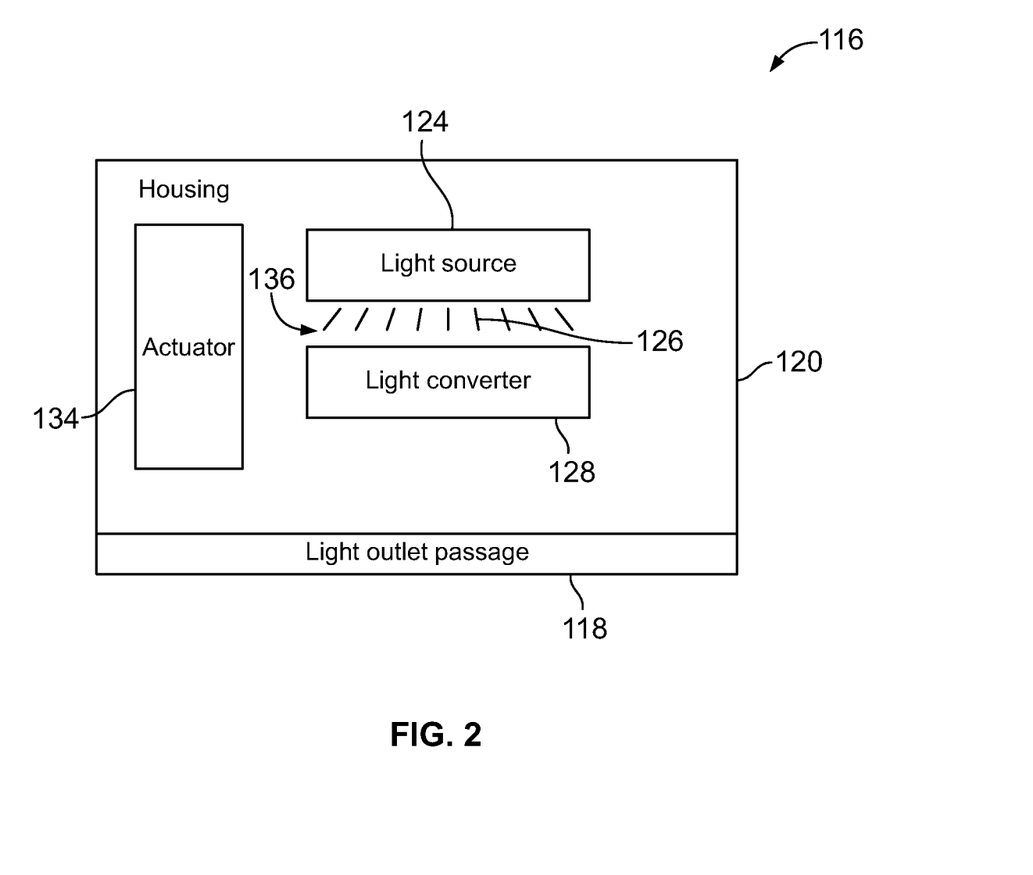
FIG. 2 illustrates a block diagram of a lighting assembly, according to an embodiment of the present disclosure.

FIG. 2 illustrates a block diagram of the lighting assembly 116, according to an embodiment of the present disclosure. As indicated, the lighting assembly 116 includes the housing 120, which contains the light source 124. The light source 124 emits light 126 at a first frequency. The actuator 134 is operatively coupled to one of the light converter 128 or the light source 124 to selectively move the light converter 128 relative to the light source 124. When the light converter 128 is outside of the light emission path 126 of the light source 124, the light 126 at the first frequency passes through the light outlet passage 118. When the light converter 128 is within the light emission path 126, the light converter 128 down-converts the emitted light from the first frequency to a second frequency that is lower than the first frequency, which then passes through the light outlet passage 118.

The light converter 128 may be positioned within the housing 120 between the light source 124 and the light outlet passage 118. For example, the light converter 128 may be disposed over the light outlet passage 118 when the light converter 128 is within the light emission path 126. In at least one other embodiment, the light converter 128 may underlay the light outlet passage 118.

Figure 3:
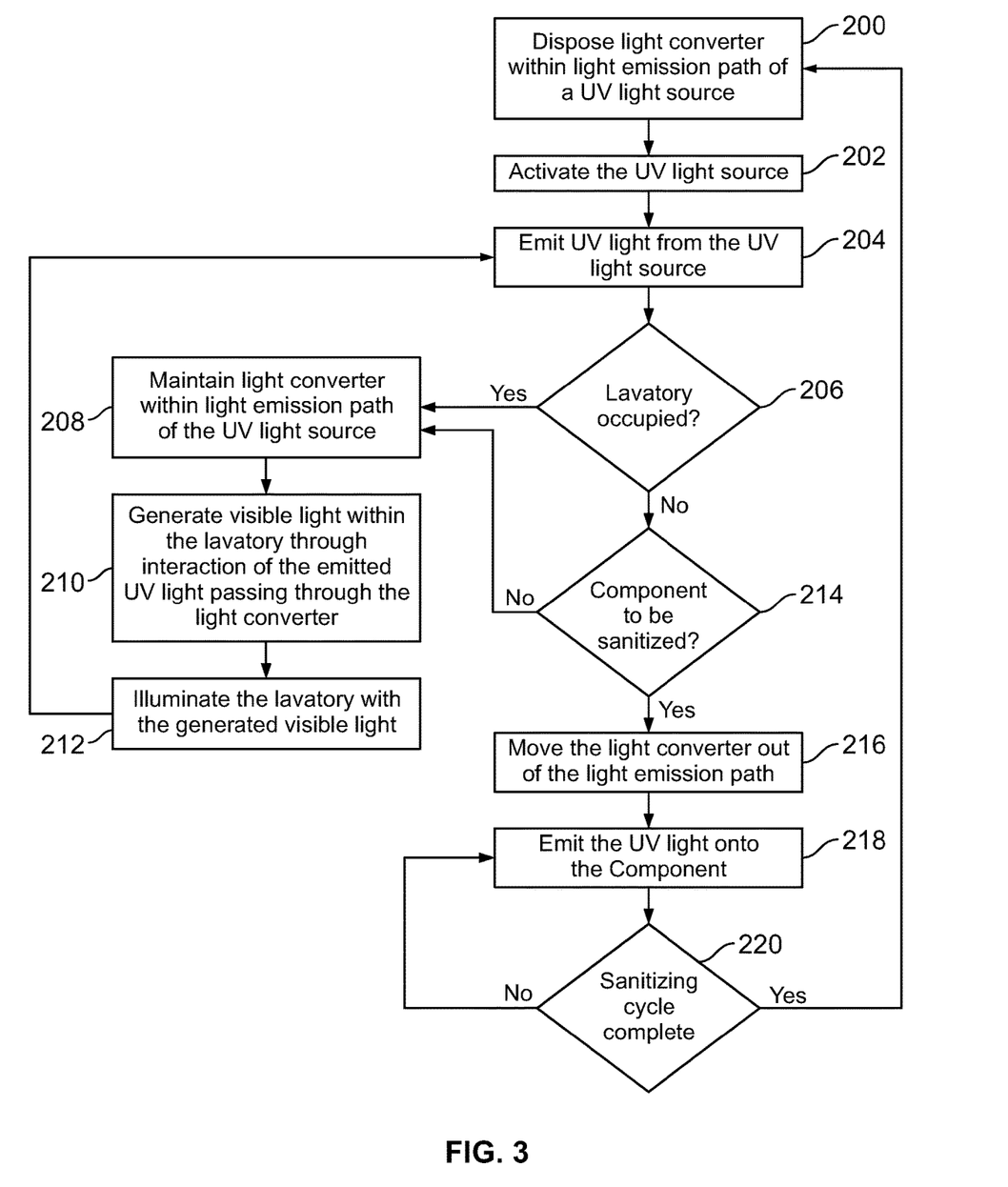
FIG. 3 illustrates a flow chart of a method of using a lighting assembly to sanitize a component within a confined space, such as a lavatory, according to an embodiment of the present disclosure.

FIG. 3 illustrates a flow chart of a method of using a lighting assembly to sanitize a component within a confined space, such as a lavatory, according to an embodiment of the present disclosure. Referring to FIGS. 1-3, the method begins at 200, at which the UV light control unit 140 operates the actuator 134 to dispose the light converter 128 within the light emission path 136 of the UV light source 124. At 202, the light control unit 140 activates the UV light source 124. At 204, UV light 126 is emitted from the activated UV light source 124.

At 206, the UV light control unit 140 determines whether the lavatory 102 is occupied. If the lavatory 102 is occupied, the method proceeds from 206 to 208, at which the UV light control unit 140 maintains the light converter 128 within the light emission path 136 of the UV light source 124. At 210, visible light is generated within the lavatory 102 through interaction of the emitted UV light 126 passing through the light converter 128. In particular, as the UV light 126 passes through the phosphor layer 132 of the light converter 128, the UV light 126 is down-converted into lower frequency visible light. At 212, the interior of the lavatory 102 is illuminated with the generated visible light. The method then returns to 204.

At 206, if the UV light control unit 140 determines that the lavatory is not occupied, the method proceeds to 214, at which the UV light control unit 140 determines whether the component 114 is to be sanitized. If the component 114 is not in need of sanitation, the method proceeds to 208.

If, however, the component 114 is in need of sanitation, the method proceeds from 214 to 216, at which the UV light control unit 140 moves the light converter 128 out of the light emission path 136 of the light source 124. As such, the UV light 126 emitted from the UV light source 124 passes through the lighting assembly 116 unimpeded, and is emitted onto the component 114 at 218, thereby sanitizing the component 114.

At 220, the UV light control unit 140 determines whether the sanitizing cycle is complete. If the sanitizing cycle is not complete, the method returns to 218. If, however, the sanitizing cycle is complete, the method returns to 200 from 220.

Figure 4:
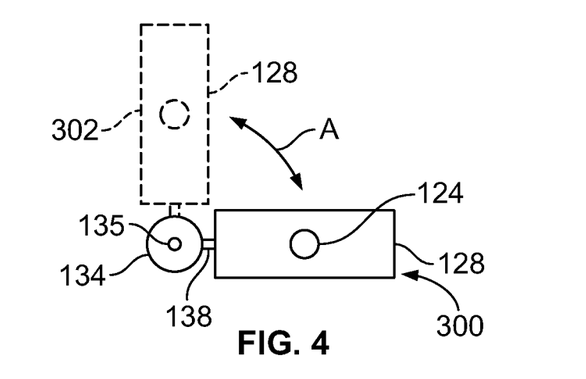
FIG. 4 illustrates a top view of an actuator coupled to a light converter, according to an embodiment of the present disclosure.

FIG. 4 illustrates a top view of an actuator 134 coupled to a light converter 128, according to an embodiment of the present disclosure. The link 138 that securely connects the actuator 134 to the light converter 128 may be one or more of a bracket(s), beam(s), clamp(s), and/or the like. The actuator 134 is configured to rotate the light converter 128 about a vertical axis 135 of the actuator 134 in the directions of arc A between a first position 300, in which the light converter 128 is underneath the light source 124 within a light emission path, and a second position 302, in which the light converter 128 is outside of the light emission path.

Figure 5:
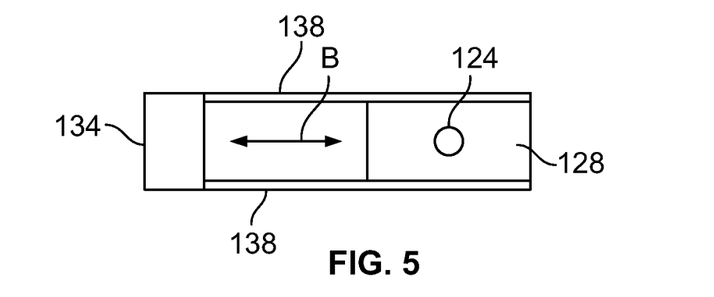
FIG. 5 illustrates a top view of an actuator coupled to a light converter, according to an embodiment of the present disclosure.

FIG. 5 illustrates a top view of an actuator 134 coupled to a light converter 128, according to an embodiment of the present disclosure. In this embodiment, the link 138 that securely connects the actuator 134 to the light converter 128 may be a track and rail system, for example. The actuator 134 is configured to push and pull the light converter 128 along the link 138 in the directions of line B between a first position, in which the light converter 128 is underneath the light source 124 within a light emission path, and a second position, in which the light converter 128 is outside of the light emission path.

Figure 6:
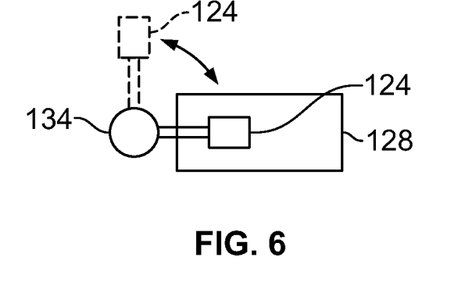
FIG. 6 illustrates a top view of an actuator coupled to a light source, according to an embodiment of the present disclosure.

FIG. 6 illustrates a top view of an actuator 134 coupled to a light source 124, according to an embodiment of the present disclosure. The embodiment of FIG. 6 is similar to that of FIG. 4, except that the actuator 134 is operatively coupled to the light source 124, while the light converter 128 remains fixed in place.

Figure 7:
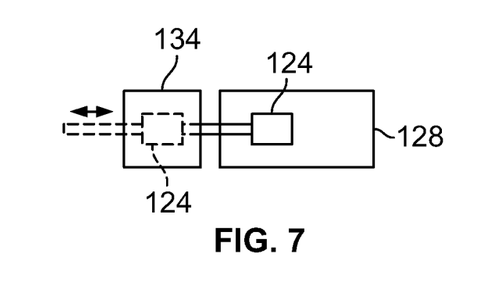
FIG. 7 illustrates a top view of an actuator coupled to a light source, according to an embodiment of the present disclosure.

FIG. 7 illustrates a top view of an actuator 134 coupled to a light source 124, according to an embodiment of the present disclosure. The embodiment of FIG. 7 is similar to that of FIG. 5, except that the actuator 134 is operatively coupled to the light source 124, while the light converter 128 remains fixed in place.

Figure 8:
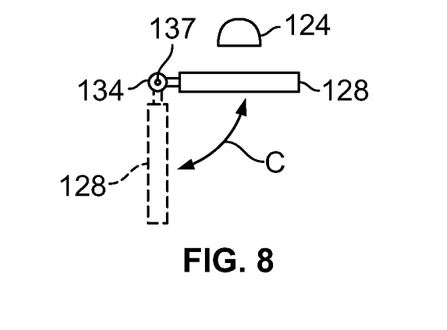
FIG. 8 illustrates a lateral view of an actuator coupled to a light converter, according to an embodiment of the present disclosure.

FIG. 8 illustrates a lateral view of an actuator 134 coupled to a light converter 128, according to an embodiment of the present disclosure. In this embodiment, the actuator 134 is configured to pivot the light converter between first and second positions about a horizontal axis 137.

Figure 13:
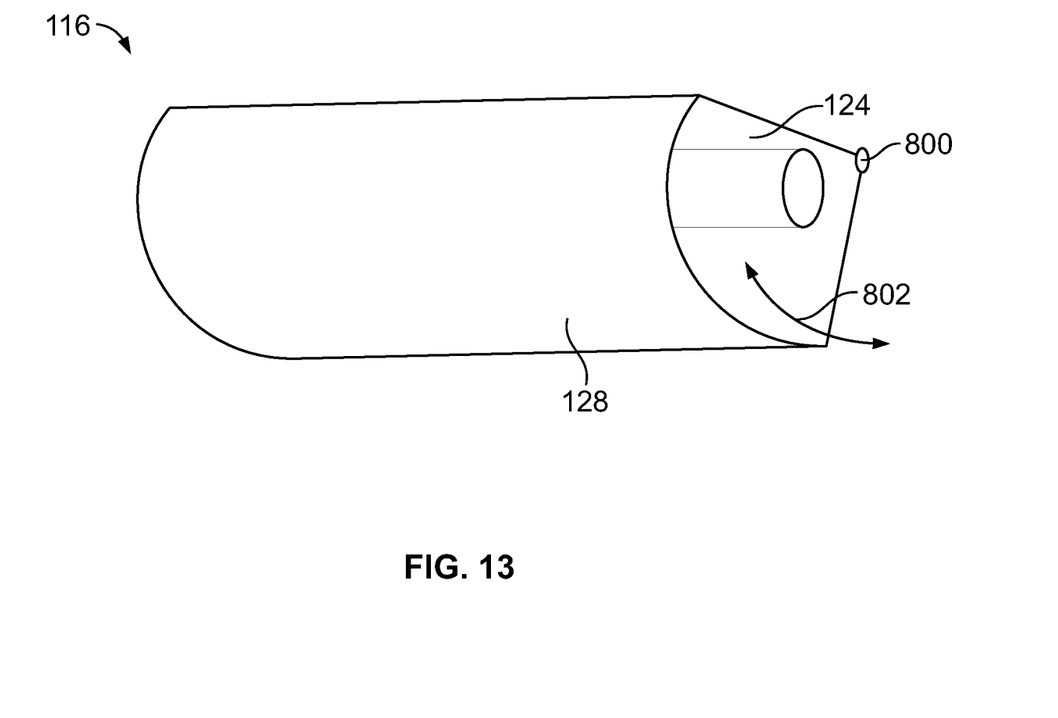
FIG. 13 illustrates a perspective bottom view of a lighting assembly, according to an embodiment of the present disclosure.

FIG. 13 illustrates a perspective bottom view of a lighting assembly 116, according to an embodiment of the present disclosure. In at least one embodiment, the light source 124 includes a UV-generating light bulb, such as an excimer light bulb. The light source 124 is positioned above an outwardly-bowed light converter 128, such as an arcuate sheet of phosphor-coated glass. The light converter 128 is coupled to a pivot axle 800 having a longitudinal axis that is parallel with a longitudinal axis of the light source 124. An actuator is configured to rotate the light converter 128 about the longitudinal axis of the pivot axle 800 in the directions of arc 802.

Figure 9:
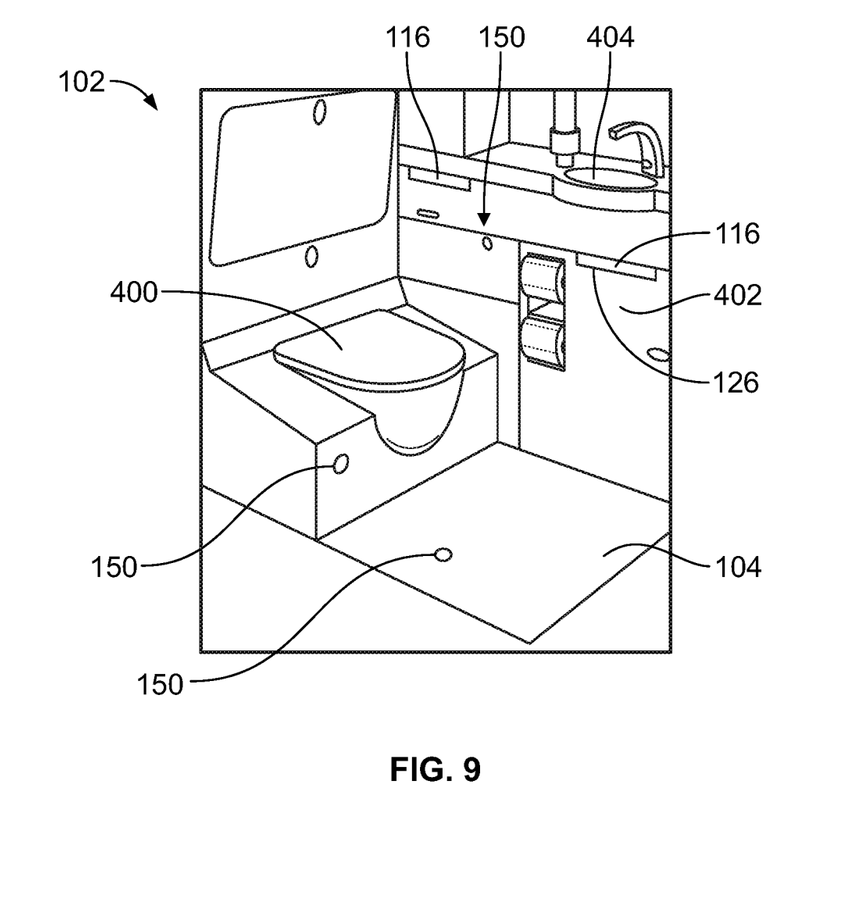
FIG. 9 illustrates a perspective internal view of a lavatory, according to an embodiment of the present disclosure.

FIG. 9 illustrates a perspective internal view of a lavatory 102, according to an embodiment of the present disclosure. The lavatory 102 is an example of the enclosed space 102 shown and described with respect to FIG. 1. The lavatory 102 may be onboard an aircraft, as described above. Optionally, the lavatory 102 may be onboard various other vehicles. In other embodiments, the lavatory 102 may be within a fixed structure, such as a commercial or residential building.

The lavatory 102 includes the floor 104 that supports a toilet 400, cabinets 402, and a sink 404. Lighting assemblies 116 are secured within the lavatory 102 and are configured to be activated during a sanitizing cycle to sanitize (for example, disinfect, sterilize, or otherwise clean) various structures within the lavatory 102, such as the toilet 400, the floor 104, the cabinets 402, and/or the sink 404. The presence sensors 130 may be secured to portions of the lavatory 102.

When the lavatory 102 is occupied, the lighting assemblies 116 are operated to emit visible light to safely illuminate the interior of the lavatory 102, as described above. During a sanitizing cycle, the lighting assemblies 116 are operated to emit sanitizing UV light, as described above.

Figure 10:
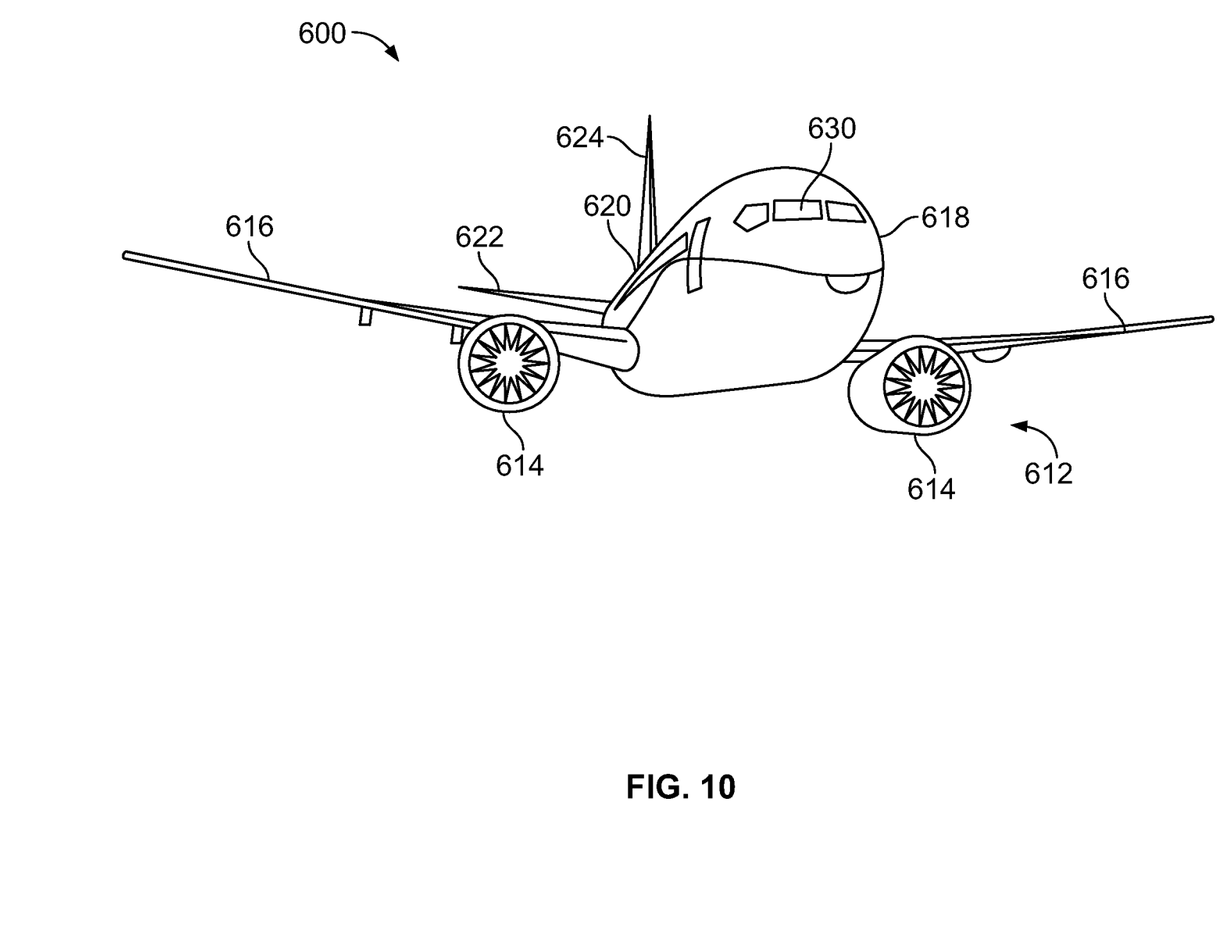
FIG. 10 illustrates a perspective front view of an aircraft, according to an embodiment of the present disclosure.

FIG. 10 illustrates a perspective front view of an aircraft 600, according to an embodiment of the present disclosure. The aircraft 600 includes a propulsion system 612 that may include two turbofan engines 614, for example. Optionally, the propulsion system 612 may include more engines 614 than shown. The engines 614 are carried by wings 616 of the aircraft 600. In other embodiments, the engines 614 may be carried by a fuselage 618 and/or an empennage 620. The empennage 620 may also support horizontal stabilizers 622 and a vertical stabilizer 624.

The fuselage 618 of the aircraft 600 defines an internal cabin, which may include a cockpit, one or more work sections (for example, galleys, personnel carry-on baggage areas, and the like), one or more passenger sections (for example, first class, business class, and coach sections), and an aft section in which an aft rest area assembly may be positioned. Each of the sections may be separated by a cabin transition area, which may include one or more class divider assemblies. Overhead stowage bin assemblies may be positioned throughout the internal cabin. The internal cabin includes one or more chambers, such as lavatories, for example. One or more UV light sanitizing systems 100 (shown and described with respect to FIG. 1) may be located within the internal cabin.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 11:
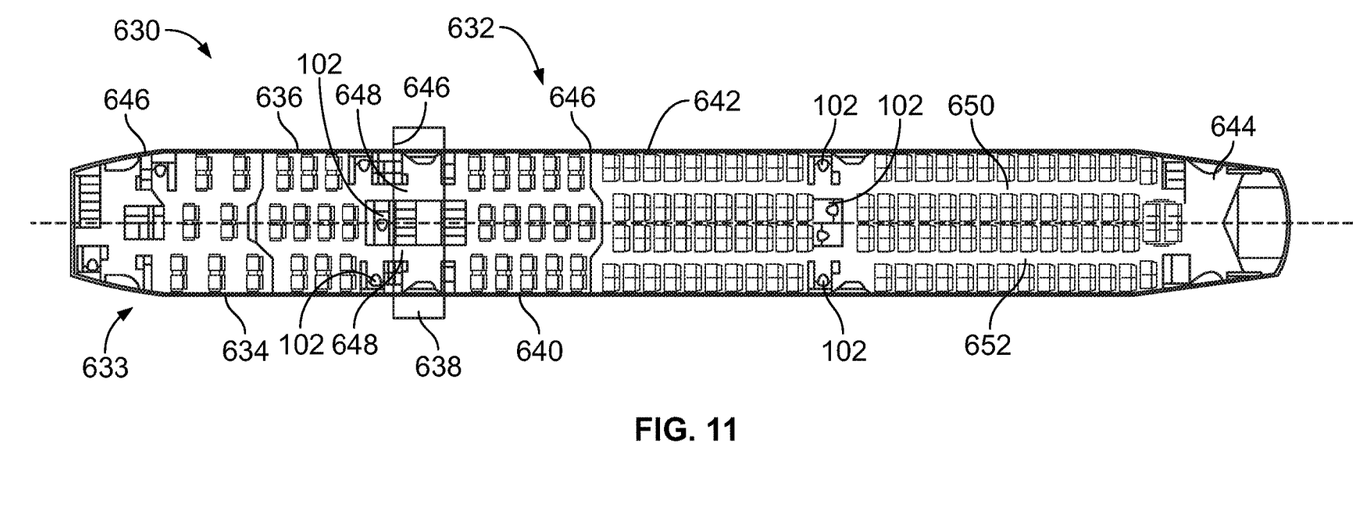
FIG. 11 illustrates a top plan view of an internal cabin of an aircraft, according to an embodiment of the present disclosure.

FIG. 11 illustrates a top plan view of an internal cabin 630 of an aircraft, according to an embodiment of the present disclosure. The internal cabin 630 may be within a fuselage 632 of the aircraft. For example, one or more fuselage walls may define the internal cabin 630. The internal cabin 630 includes multiple sections, including a front section 633, a first class section 634 (or first class suites, cabins, for example), a business class section 636, a front galley station 638, an expanded economy or coach section 640, a standard economy or coach section 642, and an aft section 644, which may include multiple enclosed spaces or chambers 102, such as lavatories and galley stations. It is to be understood that the internal cabin 630 may include more or less sections than shown. For example, the internal cabin 630 may not include a first class section, and may include more or less galley stations than shown. Each of the sections may be separated by a cabin transition area 646, which may include class divider assemblies between aisles 648.

As shown in FIG. 11, the internal cabin 630 includes two aisles 650 and 652 that lead to the aft section 644. Optionally, the internal cabin 630 may have less or more aisles than shown. For example, the internal cabin 630 may include a single aisle that extends through the center of the internal cabin 630 that leads to the aft section 644.

One or more enclosed spaces 102, such as lavatories, may be located within the internal cabin 630. UV light sanitizing systems 100 may be used to sanitize structures within the lavatories 102, such as described above.

Figure 12:
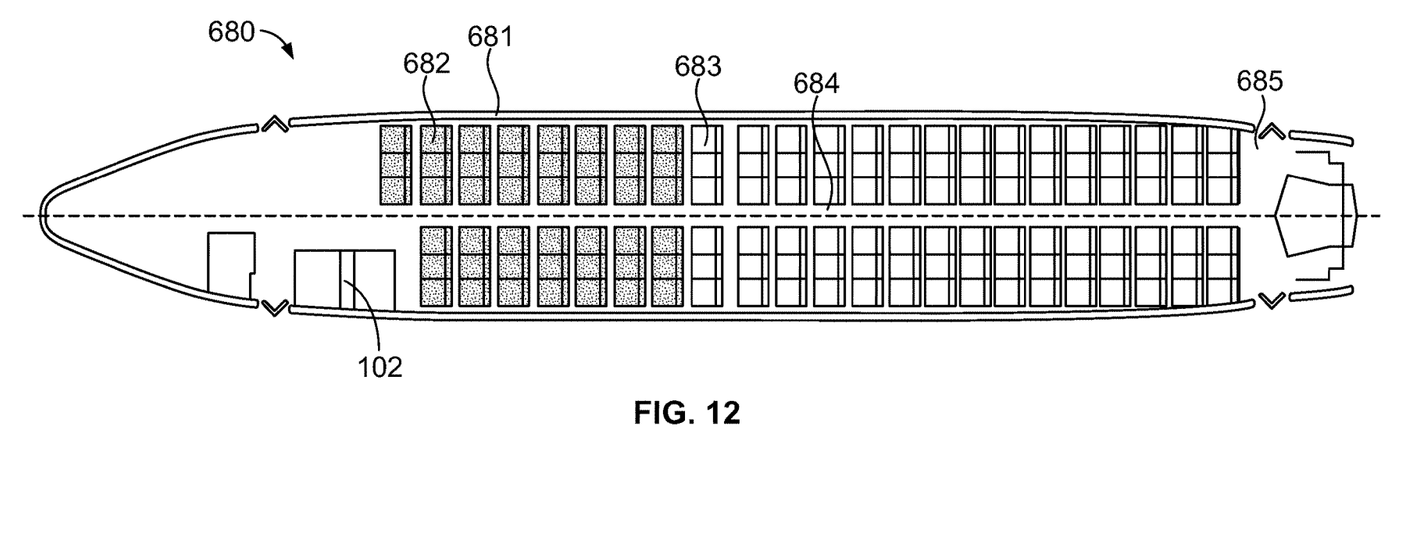
FIG. 12 illustrates a top plan view of an internal cabin of an aircraft, according to an embodiment of the present disclosure.

FIG. 12 illustrates a top plan view of an internal cabin 680 of an aircraft, according to an embodiment of the present disclosure. The internal cabin 680 may be within a fuselage 681 of the aircraft. For example, one or more fuselage walls may define the internal cabin 680. The internal cabin 680 includes multiple sections, including a main cabin 682 having passenger seats 683, and an aft section 685 behind the main cabin 682. It is to be understood that the internal cabin 680 may include more or less sections than shown.

The internal cabin 680 may include a single aisle 684 that leads to the aft section 685. The single aisle 684 may extend through the center of the internal cabin 680 that leads to the aft section 685. For example, the single aisle 684 may be coaxially aligned with a central longitudinal plane of the internal cabin 680.

One or more enclosed spaces 102, such as lavatories, may be located within the internal cabin 680. UV light sanitizing systems 100 may be used to sanitize structures within the lavatories 102, such as described above.

As described above, embodiments of the present disclosure provide systems and methods for efficiently and effectively sanitizing a surface of a component. Embodiments of the present disclosure provide systems and methods for operating a UV light assembly to sanitize a component without interfering with use of the component by an individual. Further, embodiments of the present disclosure provide systems and methods for efficiently and effectively incorporating a UV light assembly into a confined space of an aircraft lavatory.

Instead of using two separate and distinct light sources within the confined space of an aircraft lavatory, a single lighting assembly may be used to selectively emit sanitizing UV light and illuminating visible light. A light converter is used to selectively convert the UV light into visible light. In this manner, less material is used to construct the lavatory, which saves costs and reduces an overall weight of the lavatory (and therefore an aircraft into which the lavatory is positioned).

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A vehicle comprising: an internal cabin; a lavatory within the internal cabin, wherein the lavatory comprises a floor that supports a toilet and a sink: and a sanitizing system that is configured to sanitize at least one surface of the floor, the toilet, or the sink, the sanitizing system comprising a lighting assembly that is configured to selectively emit sanitizing light at a first frequency and light at a second frequency, the lighting assembly comprising:
a light source that is configured to emit the sanitizing light at the first frequency over a light emission path, wherein the light source has a first longitudinal axis;
a light converter including an outwardly-bowed sheet, wherein the light converter is coupled to a pivot axle having a second longitudinal axis that is parallel with the first longitudinal axis; and
an actuator operatively coupled to the light converter, wherein the actuator is configured to rotate the light converter about the second longitudinal axis of the pivot axle between a first position and a second position, wherein the light converter is within the light emission path in the first position, and outside of the light emission path in the second position, wherein the light converter converts the sanitizing light at the first frequency to the light at the second frequency in the first position, and wherein the sanitizing light at the first frequency is emitted from the lighting assembly when the light converter is in the second position to sanitize the at least one surface,
wherein the sanitizing system further comprises one or more presence sensors within the lavatory and in communication with a UV light control unit, wherein the one or more presence sensors are configured to detect a presence of an individual within the lavatory, wherein the UV light control unit maintains the light converter in the first position when the lavatory is occupied.

2. The vehicle of claim 1, wherein the second frequency is lower than the first frequency.

3. The vehicle of claim 1, wherein the sanitizing light at the first frequency is ultraviolet (UV) light, and wherein the light at the second frequency is visible light.

4. The vehicle of claim 1, wherein the light source is fixed in place.

5. The vehicle of claim 1, wherein the outwardly-bowed sheet of the light converter comprises an optically transparent substrate and a phosphor layer, wherein the phosphor layer is configured to down-convert the sanitizing light at the first frequency to the light at the second frequency.

6. The vehicle of claim 5, wherein the phosphor layer coats at least a portion of the substrate.

7. The vehicle of claim 5, wherein the phosphor layer is dispersed throughout the substrate.

8. The vehicle of claim 5, wherein the phosphor layer is protected inside the substrate.

9. A method of sanitizing at least one surface of a floor, toilet or sink of a lavatory within an internal cabin of a vehicle, the method comprising:
providing a light source having a first longitudinal axis;
coupling a light converter including an outwardly-bowed sheet to a pivot axle having a second longitudinal axis that is parallel with the first longitudinal axis;
emitting, from the light source, sanitizing light at a first frequency from a light source over a light emission path;
using an actuator operatively coupled to the light converter to rotate the light converter about the second longitudinal axis of the pivot axle between a first position and a second position, wherein the light converter is within the light emission path in the first position, and outside of the light emission path in the second position;
converting the sanitizing light at the first frequency with the light converter in the first position to light at a second frequency; and
emitting the sanitizing light at the first frequency from the lighting assembly onto the at least one surface of the floor, the toilet, or the sink when the light converter is in the second position to sanitize the at least one surface;
wherein the method further comprises one or more presence sensors within the lavatory and in communication with a UV light control unit, wherein the one or more presence sensors are configured to detect a presence of an individual within the lavatory, wherein the UV light control unit maintains the light converter in the first position when the lavatory is occupied.

10. The method of claim 9, wherein the second frequency is lower than the first frequency.

11. The method of claim 9, wherein the sanitizing light at the first frequency is ultraviolet (UV) light, and wherein the light at the second frequency is visible light.

12. The method of claim 9, wherein the light source is fixed in place.

13. The method of claim 9, wherein the outwardly-bowed sheet of the light converter comprises an optically transparent substrate and a phosphor layer, wherein the phosphor layer is configured to down-convert the sanitizing light at the first frequency to the light at the second frequency.

14. The method of claim 13, wherein the phosphor layer is protected inside the substrate.

15. A vehicle comprising: an internal cabin;
a lavatory within the internal cabin, wherein the lavatory comprises a floor that supports a toilet and a sink; and
at least one ultraviolet (UV) light sanitizing system that is configured to sanitize at least one surface of the floor, the toilet, or the sink, the at least one UV light sanitizing system comprising:
a lighting assembly that is configured to selectively emit sanitizing UV light and visible light, the lighting assembly comprising: (a) a light source that is configured to emit the sanitizing UV light over a light emission path, (b) a light converter, and (c) an actuator operatively coupled to one of the light source or the light converter, wherein the actuator is configured to move one of the light converter or the light source relative to the other of the light converter or the light source between a first position and a second position, wherein the light converter is within the light emission path in the first position, and outside of the light emission path in the second position, wherein the light converter converts the sanitizing UV light to the visible light in the first position, and wherein the sanitizing UV light is emitted from the lighting assembly when the light converter is in the second position; and a UV light control unit in communication with the UV light assembly, wherein the UV light control unit is configured control operation of the actuator to selectively emit the sanitizing UV light and the visible light from the UV light assembly, wherein the UV light control unit is configured to operate the UV light assembly during a sanitizing cycle in which the UV light assembly emits the sanitizing UV light onto the at least one surface to sanitize the at least one surface, wherein the UV light sanitizing system further comprises one or more presence sensors within the lavatory and in communication with the UV light control unit, wherein the one or more presence sensors are configured to detect a presence of an individual within the lavatory, wherein the UV light control unit maintains the light converter in the first position when the lavatory is occupied.

16. The vehicle of claim 15, wherein the actuator is operatively coupled to the light converter, and wherein the light source is fixed in place.

17. The vehicle of claim 15, wherein the actuator is operatively coupled to the light source, and wherein the light converter is fixed in place.

18. The vehicle of claim 15, wherein the actuator is configured to rotatably move one of the light converter or the light source relative to the other of the light converter or the light source.

19. The vehicle of claim 15, wherein the light converter comprises an optically transparent substrate and a phosphor layer.

* * * * *